United States Patent [19]

Yoshinaga et al.

[11] Patent Number: 4,879,295

[45] Date of Patent: Nov. 7, 1989

[54] N-TETRAZOLYL THIAZOLECARBOXYAMIDE DERIVATIVES AND THEIR USE

[75] Inventors: Junji Yoshinaga, Neyagawa; Takeshi Shoyaki, Suita; Takao Kakita, Toyonaka; Hiromi Ozeki, Osaka; Nobuko Sugimoto, Ashiya; Yoshiko Kato, Kobe, all of Japan

[73] Assignee: Sawai Pharmaceutical Co., Ltd., Japan

[21] Appl. No.: 98,015

[22] Filed: Sep. 17, 1987

[30] Foreign Application Priority Data

Sep. 27, 1986 [JP] Japan ................................. 61-229207
Jan. 12, 1987 [JP] Japan ................................. 62-004541
Jul. 17, 1987 [JP] Japan ................................. 62-178431

[51] Int. Cl.$^4$ .................. C07D 417/12; C07D 417/14
[52] U.S. Cl. ..................................... 514/255; 514/314; 514/326; 514/342; 514/365; 544/405; 546/167; 546/209; 546/276; 548/200
[58] Field of Search ................ 548/700; 514/365, 314, 514/326, 342; 544/405; 546/167, 276, 209

[56] References Cited

U.S. PATENT DOCUMENTS

| 4,146,631 | 4/1979 | Ford et al. ........................ 548/205 |
| 4,432,986 | 2/1984 | Erickson ........................... 548/205 |
| 4,526,979 | 7/1985 | Peet et al. ........................ 548/205 |
| 4,558,059 | 12/1985 | Kawasaki et al. ................. 548/205 |
| 4,567,193 | 1/1986 | Peet et al. ........................ 548/205 |

FOREIGN PATENT DOCUMENTS

| 0051409 | 5/1982 | European Pat. Off. . |
| 8099 | 4/1973 | Japan . |
| 167685 | 7/1986 | Japan . |
| 606019 | 3/1976 | Switzerland .................... 548/200 |

OTHER PUBLICATIONS

Hargrave, et al., Journal of Med. Chem., vol. 26, p. 1158 (1983).
Peet, et al., Journal of Med. Chem., vol. 29, p. 538 (1986).
European Search Report application No. EP 87 30 8481.
Journal of Med. Chem., "Synthesis and Quantitative Structure-Activity Relationships of Antiallergic 2-Hydroxy-N-1H-tertrazol-5-ylbenzamides and N-(2-Hydroxyphenyl)-1H-tetrazole-5-carboxyamides", Ford, et al., vol. 29, p. 538, (1986).
Journal of Med. Chem., "Antiallergic Agents. 2$^1$. N-(1-H-Tetrazol-5-yl)-6-phenyl-2-pyridinecarboxamides", Honma, et al., vol. 26, p. 1499 (1983).
Chemical Abstracts, vol. 79 (15) p. 441, No. 92204b.

Primary Examiner—Robert Gerstl
Attorney, Agent, or Firm—Scully, Scott, Murphy & Presser

[57] ABSTRACT

Compounds of the formula:

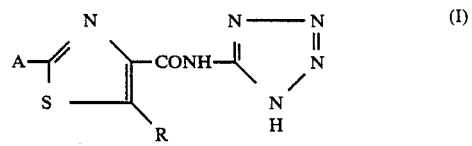

wherein
  A is a $C_{1-6}$ alkyl group, an aryl group which is unsubstituted or substituted with at least one substituent selected from hydroxy, alkoxy, aryl-($C_{1-6}$)alkoxy, $C_{1-6}$alkylcarbonyloxy, halo-($C_{1-6}$)alkyl, halogen, nitro and amino,
  or 5- or 6-membered heterocyclic group containing at least one hetero atom selected from oxygen, nitrogen and sulfur, or a condensed heterocyclic group consisting of a heterocycle as defined above and a benzene nucleus,
  these two heterocyclic groups being unsubstituted or substituted with at least one substituent selected from hydroxy, $C_{1-6}$alkyl and halogen, and R is hydrogen or a $C_{1-6}$ alkyl group, or a pharmaceutically acceptable salt thereof are nobel and useful as antiallergic.

8 Claims, No Drawings

N-TETRAZOLYL THIAZOLECARBOXYAMIDE DERIVATIVES AND THEIR USE

BACKGROUND OF THE INVENTION

1. Field of the Invention

The present invention relates to N-tetrazolyl thiazolecarboxamide derivatives having antiallergic activity, a process for preparation thereof and a pharmaceutical composition comprising the said derivatives.

Various compounds including disodium cromoglicate, chlorpheniramine maleate, tranilast etc. have been known to have the antiallergic activity and practically used on the basis of such activity. However, they have a number of deficiencies such as induction of undesirable side effects, insufficiency of peroral absorption and unsatisfactoriness of therapeutic effect. Accordingly, there has been a continuous demand for antiallergic agent which has not such deficiencies.

After an extensive study on the antiallergic agents, the present inventors have discovered that a certain group of N-tetrazolyl thiazolecarboxamide derivatives have an excellent antiallergic activity even if they administered perorally and have less side effects.

2. Related Disclosures

N-substituted phenylthiazolecarboxamide derivates wherein the substituents are alkyl, aryl, alicyclic or benzyl are disclosed in Japanese Patent Publication No. 8099/1973 (JP=B1) and U.S. Pat. No. 4,558,059. N-thiazolyl oxamic acid derivatives are disclosed in J. Med. Chem. 26, 1158–1163(1983). N-tetrazolyl benzamides are disclosed in U.S. Pat. Nos. 4,526,979, 4,567,193 and 4,146,631, J. Med. Chem. 29, 538–549(1986) and ibid, 29, 2403–2409(1086). N-tetrazolyl nicotinamides are disclosed in J. Med. Chem. 26, 1499–1504(1983). Thiazolylmethyl tetrazoles are disclosed in Japanese Patent Publication (Unexamined) No. 167685/1986(JP=A).

SUMMARY OF THE INVENTION

In one aspect, the present invention relates to a compound of the formula:

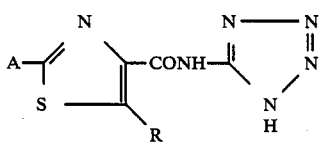

wherein
A is a $C_{1-6}$ alkyl group, an aryl group which is unsubstituted or substituted with at least one substituted selected from hydroxy, alkoxy, aryl-$(C_{1-6})$alkoxy, $C_{1-6}$alkylcarbonyloxy, halo-$(C_{1-6})$alkyl, halogen, nitro and amino,
or 5- or 6-membered heterocyclic group containing at least one hetero atom selected from oxygen, nitrogen and sulfur, or a condensed heterocyclic group consisting of a heterocycle as defined above and a benzene nucleus,
these two heterocyclic groups being unsubstituted or substituted with at least one substituent selected from hydroxy, $C_{1-6}$alkyl and halogen, and R is hydrogen or a $C_{1-6}$alkyl group,
or a pharmaceutically acceptable salt thereof.

The compounds of the above formula (I) may be prepared by (a) reacting a substituted thiazole carboxylic acid of the formula:

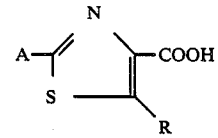

wherein A and R are as defined above, or a reactive derivative at the carboxy group thereof, with an aminotetazole of the formula:

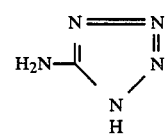

or a ractive derivative at the amino group thereof, to give a compound of formula (I), or (b) reducing a compound of the formula:

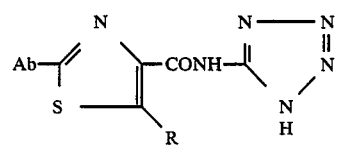

wherein Ab is an aryl group substituted at least with one nitro group, to give a compound of the formula:

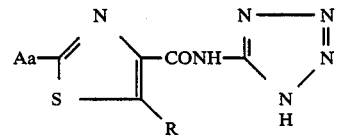

wherein Aa is an aryl group substituted at least with one amino group.

In another aspect, the present invention relates to a pharmaceutical composition, useful in treatment of allergic diseases, comprising as an active ingredient the compound of the above formula (I) or a pharmaceutically acceptable salt thereof in association with a pharmaceutically acceptable carrier, diluent or excipient.

DEATAILED DESCRIPTION OF THE INVENTION

Definitions

The terms and the definition described in this specification are illustrated in more detail as follows:

The term "$C_{1-6}$ alkyl" as a group or a moiety in $C_{1-6}$ alkylcarbonyloxy or halo-$(C_{1-6})$alkyl includes saturated straight or branched chain hydrocarbon radicals containing the number of (preferably 1–5) carbons indicated, such as methyl, ethyl, propyl, isopropyl, butyl, isobutyl, t-butyl, pentyl and hexyl.

The term "$C_{1-6}$ alkoxy" as a moiety in aryl-$(C_{1-6})$alkoxy refers to the group-O-$(C_{1-6})$alkyl wherein $(C_{1-6})$alkyl is as defined above.

The term "alkoxy" refers to the group -O-alkyl wherein alkyl includes saturated straight or branched chain hydrocarbon radical. Preferred alkyl contains 1 to 20 carbon atoms, such as methyl, ethyl, propyl, isopropyl, butyl, isobutyl, t-butyl, pentyl, hexyl, heptyl, octyl, nonyl, decyl, dodecyl, hexadecyl(cetyl) and octadecyl(stearyl).

The term "halo" as a radical or a moiety in halo-($C_{1-6}$)alkyl denotes fluoro, chloro, bromo and iodo.

The term "halo-($C_{1-6}$)alkyl" includes $C_{1-6}$ alkyl substituted at least with one, usually 1 to 5 and preferably 1 to 3 halogen, such as chloromethyl, trifluoromethyl and 2,2,2-trichloroethyl.

The term "aryl" as a group or a moiety in aryl-($C_{1-6}$)alkoxy includes monocyclic aryl such as unsubstituted phenyl and $C_{1-6}$ alkylphenyl wherein $C_{1-6}$ alkyl is as defined above (such as tolyl, xylyl, cumenyl etc.) and bicyclic aryl such as biphenyl and naphthyl unsubstituted or substituted with $C_{1-6}$ alkyl wherein $C_{1-6}$ alkyl is as defined above. These aryl may be unsubstituted or substituted with at least one, usually 1 to 5 and preferably 1 to 3 substituents selected from hydroxy, alkoxy (e.g. $CH_3O-$ or $C_{18}H_{36}O-$), aryl-($C_{1-6}$)alkoxy (e.g. $C_6H_5CH_2O-$), $C_{1-6}$ alkylcarbonyloxy (e.g. $CH_3COO-$), halo-($C_{1-6}$)alkyl (e.g. $CF_3-$), halogen (e.g. Cl— or Br—), nitro and amino. When the aryl has two or more substituents, they may be the same or different.

The term "5- or 6-membered heterocyclic group containing at least one hetero atom selected from oxygen, nitrogen and sulfur" includes 5-membered heterocyclic groups containing at least one hetero atom as defined above, such as furyl, thienyl, pyrrolyl, imidazolyl, oxazolyl, thiazolyl, triazolyl, tetrazolyl etc. and 6-membered heterocyclic groups containing at least one hetero atom as defined above, such as pyridyl, pyrazinyl, pyridazinyl, oxazinyl, thiazinyl, triazinyl etc.

The term "condensed heterocyclic group consisting of a heterocyclic group as defined above and a benzene nucleus" includes condensed heterocyclic groups consisting of the 5-membered heterocyclic group as defined above and a benzene nucleus, such as indolyl, indazolyl etc. and condensed heterocyclic groups consisting of the 6-membered heterocyclic group as defined above and a benzene nucleus, such as quinolyl, isoquinolyl, quinazolinyl, benzothiazinyl etc.

The above defined heterocyclic groups may be unsubstituted or substituted with at least one, usually 1 to 5 and preferably 1 to 3 substituents selected from hydroxy, $C_{1-6}$ alkyl (e.g. $CH_3-$ or $C_2H_5-$) and halogen (e.g. Cl— or Br—). When the heterocyclic groups have two or more substituents, they may be the same or different.

The 1H-tetrazolyl group of the formula:

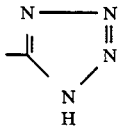

is well known to lie in tautomeric relation with a 2H-tetrazolyl group of the formula:

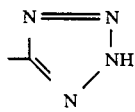

Accordingly, it is to be understood that both of the said groups are substantially the same, and the tautomers consisting of such groups are regarded as the same compounds. Therefore, both of the tautomeric forms of the compounds having such groups in their molecule are included in the scope of this invention and designated inclusively with one expression "1H-tetrazolyl" only for the convenient sake throughout this specification.

Suitable "pharmaceutically acceptable salt" includes conventional non-toxic salt, and may be a salt with an inorganic base, for example, a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amino salt (e.g. trimethylamine salt, triethylamine salt, procaine salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), a basic amino acid salt (e.g. arginine salt, lysine salt, etc.) and the like. These salts can be prepared by the conventional process, for example from the corresponding acid and base or by salt interchange.

The process for preparing the compound (I) is explained in details in the following.

(a) The compound (I) can be obtained by reacting the compound (II) or reactive derivative at the carboxy group thereof with the compound (III) or reactive derivatives at the amino group thereof.

The reactive derivative at the carboxy group of the compound (II) includes acid halides, acid anhydrides, activated esters and activated amides. Among the acid halides, acid chloride is the most frequently used. Examples of the acid anhydrides include dialkylphosphoric acid mixed anhydride, dialkylphosphorus acid mixed hydride, alkylcarbonic acid mixed anhydride, aliphatic carboxylic acid (e.g. pivalic acid, trichloroacetic acid) mixed anhydride etc. Examples of the activated esters include methyl ester, ethyl ester, cyanomethyl ester, p-nitrophenyl ester, an ester with N-hydroxysuccinimide etc. Examples of the activated amides include an amide with imidazole, dimethylimidazole or triazole.

The reactive derivative at the amino group of the compound (III) includes a Schiff's base with an aldehyde (e.g. acetaldehyde, isophentanal, benzaldehyde), a reaction product with a silyl compound (e.g. trimethylsilyl chloride, trimethylsilylacetamide), a reaction product with a phosphorus compound (e.g. phosphorus trichloride, phosphorus oxychloride).

When the compound (II) is used in the form of carboxylic acid, it is advantageous to carry out the reaction in the presence of condensing agent which may be any one conventionally used in the peptide synthesis. Examples of the condensing agent include halogenating agents such as $SOCl_2$, $SO_2Cl_2$, $PCl_3$, $PCl_5$, $POCl_3$, $PBr_3$, or N,N'-dicyclohexyl carbodiimide (DCC), N-cyclohexyl-N'-morpholinoethyl carbodiimide, N,N'-diisopropyl carbodiimide, $ClCO_2CH_3$, $ClCO_2C_2H_5$, $BrCO_2CH_3$, $(CH_3CO)_2O$, N-ethylbenzisoxazolium salts, 2-chloro-1-methylpyridinium salt, N,N'-carbonyl diimidazole (CDI), etc.

The reaction may be carried out without the solvent but is usually carried out in an inert solvent. Examples of the solvent include dioxane, methylene chloride, chloroform, ether, tetrahydrofuran (THF), acetone, dimethylformamide (DMF), dimethylsulfoxide (DMSO), pyridine, benzene, toluene, xylene etc.

A preferable example of operation is as follows.

The acid (II) is dissolved in an inert solvent and a condensing agent is added thereto. When the condensing agent is a halogenating agent, the addition is preferably carried out under ice-cooling, while other agent may be added either under ice-cooling or without cooling (i.e., at ambient temperature). The reaction mixture is kept at ambient temperature or elevated temperature such as reflux point for 0.5-3 hours. Then the activated acid thus formed is treated with the amine (III) with or without isolation. This reaction may be conducted in an inert organic solvent and, if necessary, in the presence of a base to form the desired compound (I). The base may be any one which can capture hydrogen halide, such as a tertiary amine (e.g. triethylamine or dimethylaniline) and the amine (III) can also serve as the base. The inert solvent may be the same as that used in the former step. A satisfactory yield can be obtained when the reaction is carried out at a temperature from ambient temperature up to the boiling temperature for 0.5-5 hours.

(b) The compound (Ia) can be obtained by reducing the compound (Ib) according to the conventional method.

The reduction may either be effected by catalytic reduction or by chemical reduction.

The catalytic reduction is carried out by reacting the compound (Ib) with hydrogen in a solvent such as methanol, ethanol, dioxane etc. in the presence of metal catalyst for catalytic reduction such as platinum oxide, palladium on carbon, rhodium on alumina, Raney nickel etc. the chemical reduction can be effected by using a combination of a metal and an acid or using a reducing agent.

The starting acid (II) can be prepared, for example according to the known methods, by the following process A or B.

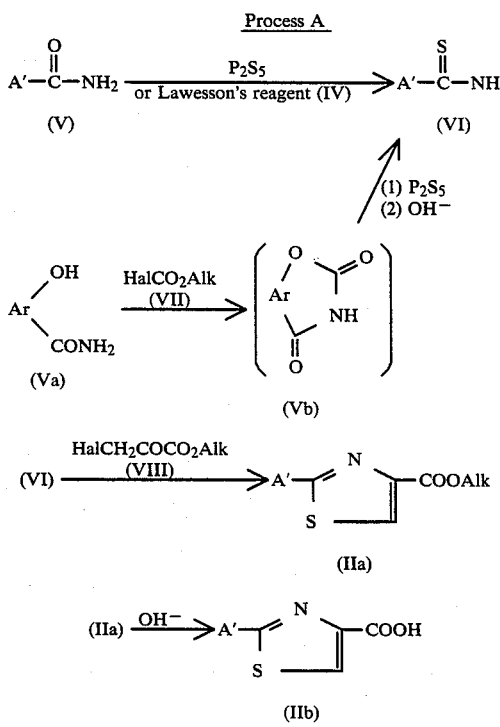

In the above scheme, A' has the same meanings as A excepting free $NH_2$ as the substituent, Ar is aryl, Alk is alkyl (preferably lower alkyl), and Hal is halogen (preferably Cl or Br).

The process A is applicable to the preparation of the compound (II) wherein R is hydrogen. Thus, in the step (i), the compound (V) is treated with $P_2S_5$ or the Lawesson's reagent [2,4-bis(4-methoxyphenyl)-1,2,3,4-dithiaphosphetane-2,4-dithione] according to the conventional method to form the compound (VI). Alternatively, when the group A' in the compound (V) is aryl group having an OH group located at the ortho-position to the group $CONH_2$, the compound (Va) is treated with the haloformate (VII) (e.g., ethyl chloroformate) to form the cyclic intermediate (Vb), which in turn is treated with $P_2S_5$ and then with aqueous alkali to give the compound (VI), according to the step (i') (cf. Pharmazie, 21, 161-166(1966). In the step (ii), the compound (VI) is reacted with the compound (VIII) (e.g. ethyl bromopyruvate) according to the conventional process to form the compound (IIa). In the step (iii), the compound (IIa) is hydrolyzed (preferably with alkali) to afford the compound (IIb).

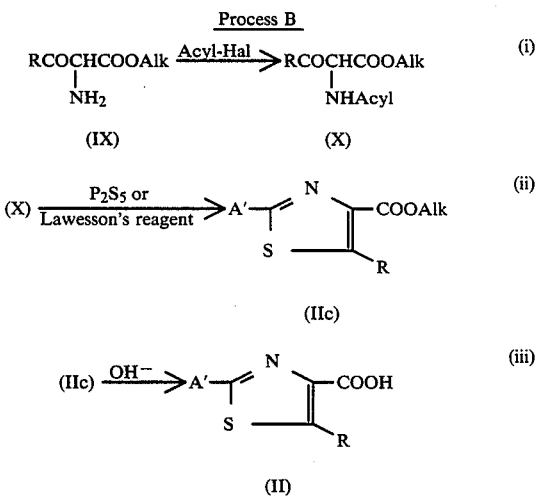

The process B is particularly suitable to the preparation of the compound (II) wherein R is $C_{1-6}$ alkyl. Thus, in the step (i), the compound (IX) is acylated to form the compound (X), which, in step (ii), is treated with $P_2S_5$ or the Lawesson's reagent to give the compound (IIc). The compound (IIc) is hydrolyzed to afford the compound (II). The compound (II) having alkoxy or $C_{1-6}$ alkylcarbonyloxy as the substituent is prepared by starting with the compound having hydroxy as the substituent and converting the hydroxy into alkoxy or alkylcarbonyloxy before or after, respectively, the step (iii) of the process A and B.

Administration

The compound (I) of the present invention has a potent antiallergic activity and therefore useful as a medicament for preventing or treating allergic diseases.

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compound (I) may vary from and also depend upon the age and conditions of the patient, a kind and degree of disease, and further a kind of the active compound (I) to be applied, an average single dose of about 0.5-50 mg/kg of the active compound (I) conveniently administered in 2-4 divided dosages a day or in a sustained release form is sufficient for treating allergic diseases.

Following preparations and examples are given only for explanation of this invention in more detail.

PREPARATION 1

2-(2-Hydroxyphenyl)-4-thiazolecarboxylic acid (Process A)

(Step 1')

Into a mixed solvent consisting of dry pyridine (36 ml) and dry acetonitrile (22 ml) was dissolved. 2-hydroxybenzamide (10 g) and ethyl chloroformate (7.8 ml) was added dropwise to the mixture under cooling, according to the method described in Pharmazie, 21, 161–166(1966). Then, the mixture was heated up to 120° C. (bath temperature), partly concentrated and refluxed for 3 hours. The reaction mixture was poured into water and acidified with concentrated hydrochloric acid. The produced precipitates were filtered and recrystallized from methanol-water to give 2,4-dihydro-1,3-benzoxadine-2,4-dione (10 g). The product (10 g) was dissolved in dry dioxane (300 ml), treated with $P_2S_5$ (12.6 g) and heated at 90° C. for 4 hours. The reaction mixture was filtered with suction and the filtrate was partly concentrated. The residue was combined with water and extracted with ethyl acetate. The extract was dried, concentrated, and the residue was washed with n-hexane to give the thio-compound as yellow solids (12 g). The thio-compound was treated with 1N-KOH (245 ml) and heated at 80° C. for 15 minutes. Then the reaction mixture was acidified with 1N-HCl under ice-cooling. The produced solids were sucked and recrystallized from water to give 2-hydroxy thiobenzamide (4.77 g), m.p. 119°–120° C. (literature, 119°–120° C., Pharmazie, 21, 161-166 (1966)). (Steps ii and iii)

Ethyl bromopyruvate (3 ml) was dissolved in dry ethanol (68 ml) and 2-hydroxythiobenzamide (3.0 g), dissolved in dry ethanol (40 ml), was added dropwise thereto, according to the method described in Agr. Biol. Chem., 34, 780–783 (1970). After refluxing for 1 hour, the reaction mixture was concentrated, the residue was treated with 4% aqueous sodium carbonate and extracted with ethyl acetate. The extract was concentrated after drying and the residue was purified by silica gel column chromatography to give the ester (4.47 g). Then the ester was hydrolyzed in methanol (90 ml) at 60° C. for 30 minutes using aqueous KOH (6.0 g KOH and 27 ml $H_2O$). After removing the solvent, the residue was treated with water, acidified, and the produced solids were filtered and recrystallized from methanol to give 2-(2-hydroxyphenyl)-4-thiazolecarboxylic acid (3.3 g), m.p. 268°–269° C. (literature, 271°–272° C., Agr. Biol. Chem. 34, 780-783 (1970)).

PREPARATION 2

2-(3-Methoxyphenyl)-4-thiazolecarboxylic acid (Process A)

(Steps i, ii and iii)

A suspension of 3-methoxybenzamide (3.5 g) in dry dioxane (110 ml) was heated to 90° C. until complete dissolution occured. To the solution was added $P_2S_5$ (5 g) and the mixture was heated at 90°-110° C. for 20 minutes. Then, the reaction mixture was poured into ice-water and extracted with ethyl acetate. The extract was washed with water, dried and concentrated to give thio-compound (4.0 g) as a red oil. A solution of the thio-compound (4.0 g) in dry ethanol (50 ml) was added dropwise to a solution of ethyl bromopyruvate (3.44 ml) in dry ethanol (36 ml) and the mixture was refluxed for 1.5 hours. The solvent was removed and the residue was treated with water and 4% aqueous sodium carbonate. The mixture was extracted with ethyl acetate. The extract was washed with water, dried and concentrated to give the ester (6.2 g). The ester (6.2 g) was dissolved in methanol (80 ml), treated with aqueous KOH (3.77 g KOH and 23 ml $H_2O$) and heated at 60° C. for 30 minutes to effect hydrolysis. The supernatant was decanted and concentrated. The residue was treated with water, acidified with 2N-HCl and extracted with ethyl acetate. The extract was washed with water, dried and concentrated to leave residue, which was recrystallized from a mixed solvent of ethyl acetate-petroleum ether in the presence of activated charcoal to give the desired compound (1.32 g, 25% from 3-methoxybenzamide) as yellow solid, m.p. 132°–133° C.

IR(KBr, cm$^{-1}$): 1700, 3200–2100. $^1$H-NMR(DMSO-d$_6$, δ): 3.83 (3H, s, —OC$\underline{H}_3$), 6.93-7.47 (4H, m, Ar-$\underline{H}$), 8.40 (1H, s, thiazole).

PREPARATION 3

2-(4-Methoxyphenyl)-5-methyl-4-thiazolecarboxylic acid (Process B)

(Steps i, ii and iii)

Ethyl 2-amino-3-oxobutanoate hydrochloride (1 g) was suspended in dry methylene chloride (30 ml) and dissolution was effected with addition of triethylamine (1.69 ml). After adding 4-methoxybenzoyl chloride (0.91 ml) dropwise under cooling, the reaction mixture was allowed to warm up to room temperature and to react for 20 minutes. The mixture was treated with water and extracted with methylene chloride. The extract was washed with water, 1N-HCl, 4% aqueous sodium bicarbonate and saturated aqueous NaCl, dried (anhydrous $Na_2SO_4$) and concentrated. The residue was dissolved in developing solvent (benzene:ethyl acetate=4:1) and applied on a silica gel column. The first fraction (unpurities) was discarded and the following fraction was pooled and concentrated to give ethyl 2-(4-methoxybenzamido)-3-oxobutanoate (1.28 g, 83%) as white solid, m.p. 67°–69° C.

The obtained product, ethyl 2-(4-methoxybenzamide)-3-oxobutanoate (1.28 g) was dissolved in dioxane (40 ml). To this solution was added Lawesson's reagent (3.8 g) and the solution was heated at 60° C. for 4 hours. The insoluble matters in the reaction mixture was removed by suction and the filtrate was concentrated. The residue was dissolved in chloroform and purified by silica gel chromatography (hexane:ethyl acetate=7:3). The first fraction was concentrated to give ethyl 2-(4-methoxyphenyl)-5-methyl-4-thiazolecarboxylate (1.1 g, 87%) as pale pink solid, m.p. 65°–66° C.

Ethyl 2-(4-methoxyphenyl)-5-methyl-4-thiazolecarboxylate (1.1 g) was dissolved in methanol (30 ml), treated with 1N aqueous KOH (11.9 ml) and heated at 50° C. for 30 minutes. The reaction mixture was concentrated. The residue was treated with water and acidified with 2N-HCl to pH 2. The produced solids were collected on a filter, washed with water and recrystallized from methanol-water to give the desired 2-(4-methoxyphenyl)-5-methyl-4-thiazolecarboxylic acid (779 mg, 79%), m.p. 166°-168° C.

IR (KBr, cm$^{-1}$): 3200-2100, 1680.

$^1$H-NMR (DMSO-d$_6$, δ): 2.73 (3H, s, —CH$_3$), 3.80 (3H, s, —OCH$_3$), 7.00 (2H, d, benzene ring), 7.77 (2H, d, benzene ring).

PREPARATION 4

2-(2-methoxyphenyl)-4-thiazolecarboxylic acid (Processes A and B)

(Methylation, step iii)

Ethyl 2-(2-hydroxyphehyl)-4-thiazolecarboxylate (1.58 g) and potassium carbonate (875 mg) were suspended in a mixed solvent of dry acetone (20 ml) and dry DMF (10 ml) and methyl iodide (0.47 ml) was added dropwise thereto. The mixture was allowed to react at 40°-60° C. for 1 hours, poured into ice-water and extracted with ethyl acetate. The extract was washed with water, dried and concentrated to give methylated product (1.63 g, m.p. 86°-87° C.). The methylated product was added to a solution of KOH (1.88 g) in a mixed solvent of methanol (30 ml) and water (6 ml) and hydrolyzed at 60° C. for 30 minutes. After removing methanol, the residue was treated with water and acidified with 2N—HCl. The produced gummy solid was recrystallized from a mixed solvent of methanol and water to give the desired compound (1.27 g), m.p. 182°-184° C.

IR (KBr, cm$^{-1}$): 1680, 3200.

$^1$H-NMR (DMSO-d$_6$, δ): 4.00 (3H, s, —OCH$_3$), 6.06-8.33 (4H, m, Ar-H), 8.37 (1H, s, thiazole), 13.10 (1H, br-s, —COOH).

PREPARATION 5

2-(2-acetoxyphenyl)-4-thiazolecarboxylic acid (Processes A and B)

(Acetylation)

To a solution of 2-(2-hydroxyphenyl)-4-thiazolecarboxylic acid (900 mg) dissolved in dry pyridine (15 ml) was added dropwise acetic anhydride (0.461 ml) under ice-cooling. The mixture was allowed to warm up to room temperature and to react for additional 1.5 hours. Then the solvent was removed and the residue was treated with water, acidified with 2N—HCl and extracted with ethyl acetate. The extract was washed with water, dried and concentrated to give the desired compound, 2-(2-acetoxyphenyl)-4-thiazolecarboxylic acid (992 mg), m.p. 189°-191° C. (recrystallized from CHCl$_3$·n-hexane).

IR (KBr, cm$^{-1}$): 3200-2100, 1760, 1710.

$^1$H-NMR (DMSO-d$_6$, δ): 2.40 (3H, s, —COCH$_3$), 7.07-8.30 (4H, m, Ar-H), 8.47 (1H, s, thiazole)

PREPARATION 6

2-(3-Hydroxy-2-pyridyl)-4-thiazolecarboxylic acid (Process A)

(Step i)

A suspension of 3-hydroxypicolinamide (1 g) and Lawesson's reagent (2 g) in dry dioxane (75 ml) was allowed to react under Argon atmosphere at 95° C. for 4 hours. Then, insoluble solids in the reaction mixture was filtered off with suction and the filtrate was concentrated. The residue was dissolved in methylene chloride and purified by silica gel column chromatography (ethyl acetate:n-hexane=1:1). The second yellow fraction was concentrated. the residual solids were recrystallized from CHCl$_3$-n-hexane to give yellow crystals of 3-hydroxythiopicolinamide (546 mg, 46%), m.p. 150°-151° C.

(Step ii)

A solution of 3-hydroxythiopicolinamide (500 mg) in dry ethanol (25 ml) was added dropwise to a solution of ethyl bromopyruvate (0.542 ml) in dry ethanol (20 ml) under nitrogen atmosphere and the mixture was refluxed for 2 hours. The solvent was removed from the reaction mixture, and the residue was treated with water, neutralized with 4% aqueous sodium carbonate and extracted with ethyl acetate. The organic layer was washed with saturated aqueous NaCl, dried (anhydrous Na$_2$SO$_4$) and concentrated. The residue was purified by silica gel column chromatography (ethyl acetate:benzene=1:9). The second fraction was concentrated. The produced solids were recrystallized from methanol-water to give yellowish crystals of ethyl 2-(3-hydroxy-2-pyridyl)-4-thiazole carboxylate (260 mg, 32%), m.p. 131°-134° C.

(Step iii)

To a solution of ethyl 2-(3-hydroxy-2-pyridyl)-4-thiazolecarboxylate (350 mg) dissolved in ethanol (7 ml) at 80° C. was added a solution of potassium hydroxide (436 mg) in water (5.5 ml) and the mixture was allowed to react at the same condition for 30 minutes. Then the reaction mixture was nuetralized with 1N—HCl under ice-cooling. The resulting solids were sucked off and dried to give yellowish crystals of 2-(3-hydroxy-2-pyridyl)-4-thiazolecarboxylic acid (287 mg, 92%), m.p. above 300° C.

IR (KBr, cm$^{-1}$): 3700-2000, 1660.

MS (m/z): 289 (M$^+$).

PREPARATION 7

2-(2-furyl)-4-thiazolecarboxylic acid (Process A).

(Step i)

To a solution of 2-furancarboxamide (1.5 g) in dry dioxane (80 ml) was added P$_2$S$_5$ (3.0 g) and the mixture was heated to 55° C. for 1.5 hours. Then, the reaction mixture was treated with water and extracted three times with ethyl acetate. The organic layer was washed with saturated aqueous NaCl, dried (anhydrous Na$_2$SO$_4$) and concentrated to give yellow crystals of 2-furan-thiocarboxamide (1.63 g).

(Step ii)

To a solution of 2-furan-thiocarboxamide (1.63 g) dissolved in dry ethanol (65 ml) with heating was added ethyl bromopyruvate (1.97 ml) and the mixture was refluxed for 30 minutes. Then the solvent was removed from the reaction mixture, and the residue was treated with water, neutralized with 4% aqueous sodium carbonate and extracted three times with ethyl acetate. The organic layer was washed with saturated aqueous NaCl, dried (anhydrous Na$_2$SO$_4$) and concentrated to give yellowish crystals of ethyl 2-(2-furyl)-4-thiazolecarboxylate (3.12 g).

(Step iii)

To a solution of ethyl 2-(2-furyl)-4-thiazole carboxylate (3.12 g) in methanol (30 ml) was added dropwise 1N aqueous potassium hydroxide (38.58 ml) and the mixture was at 55° C. for 15 minutes. Then the solvent was removed from the reaction mixture, and the residue was treated with water and acidified with 2N-HCl under ice-cooling. The resulting solids were sucked, washed with water and dried to give yellowish crystals of 2-(2-furyl)-4-thiazole carboxylic acid (1.16 g, yeild 46%), m.p. 257°–265° C.

IR(KBr, cm$^{-1}$): 3700–3200 3100, 1750, 1600.

$^1$H-NMR(DMSO-d$_6$, δ): 6.65 (1H, dd, furyl-4-$\underline{H}$), 7.15 (1H, d, furyl-3-$\underline{H}$), 7.82 (1H, d, furyl-5-$\underline{H}$), 8.12 (1H, s, thiazole-$\underline{H}$).

PREPARATION 8

2-(5-methyl-2-thienyl)-5-methyl-4-thiazolecarboxylic acid (Process B)

(Step i)

To a suspension of 5-methyl-2-thiophene-carboxylic acid (1.74 g) in dry benzene (50 ml) was added thionyl chloride (4.41 ml) and the mixture was refluxed for 1.5 hours. Then the solvent was removed from the reaction mixture, the residue was treated with dry benzene, which was then evaporated, and the procedure was repeated with dry toluene. The residue was dissolved in dry methylene chloride (10 ml) and the obtained solution was added dropwise to a solution of ethyl 2-amino-3-oxo-butanoate (2 g) and triethylamine (3.07 ml) in dry methylene chloride (50 ml) under ice-cooling. Then, the mixture was heated to room temperature and allowed to react for 30 minutes. The reaction mixture was treated with water and extracted with washed methylene chloride. The organic layer was washed with water, dried (anhydrous Na$_2$SO$_4$) and concentrated. The residue was purified by silica gel column chromatography (benzene:ethyl acetate=4:1). The first fraction containing impurities was discarded and the following fraction was concentrated to give yellowish crystals of ethyl 2-(5-methyl-2-thienylcarboxamide)-3-oxo-butanoate (1.84 g).

(Step ii)

To solution of ethyl 2-(5-methyl-2-thienylcarboxamido)-3-oxo-butanoate (1.84 g) in dry dioxane (80 ml) was added Lawesson's reagent (5.7 g) and heated to 80° C. for 2 hours. Then, the insoluble solids in the reaction mixture were sucked off and the solvent was removed from the filtrate. The residue was dissolved in chloroform and purified by silica gel column (n-hexane:ethyl acetate=4:1). The first fraction containing impurities was discarded and the following fraction was concentrated to give yellowish crystals of ethyl 2-(5-methyl-2-thienyl)-5-methyl-4-thiazolecarboxylate (1.5 g, yield 51%).

(Step iii)

To a solution of ethyl 2-(5-methyl-2-thienyl)-5-methyl-4-thiazolecarboxylate (1.47 g) in methanol (100 ml) was added 1N aqueous potassium hydroxide (16.5 ml) and the mixture was heated at 60° C. for 40 minutes. Then the solvent was removed from the reaction mixture. The residue was treated with water and acidified with 2N hydrochloric acid under ice-cooling. The deposited solids were filtered and washed with water, recrystallized from methanol-water to give yellowish crystals of 2-(5-methyl-2-thienyl)-5-methyl-4-thiazolecarboxylic acid (1.06 g, yield 80%), m.p. 160°–161° C.

IR (KBr, cm$^{-1}$): 1670.

$^1$H-NMR (DMSO-d$_6$, δ): 2.50 (3H, s, C$\underline{H}_3$ on thienyl), 2.70 (3H, s, C$\underline{H}_3$ on thiazole), 6.75 (1H, m, thienyl-4-$\underline{H}$), 7.27 (1H, d, thienyl-3-$\underline{H}$).

EXAMPLE 1

2-(2-Methoxyphenyl)-N-(1H-tetrazole-5-yl)-4-thiazolecarboxamide

A solution of 2-(2-methoxyphenyl)-4-thiazolecarboxylic acid (250 mg) and N,N'-carbonyldiimidazole (CDI, 207 mg) in dry DMF (2.5 ml) was allowed to react with stirring at room temperature for 1 hour. Then a solution of 5-aminotetrazole (109 mg) in dry DMF (1.5 ml) was added dropwise thereto and allowed to react at 70° C. for 2 hours. The solvent was removed from the mixture, and the residue was treated with water and acidified with 2N-HCl. The produced solids were filtered, washed with water, treated with stirring with ether, filtered again and dried to give white solids of the desired 2-(2-methoxyphenyl)-N-(1H-tetrazole-5-yl)-4-thiazolecarboxamide (255 mg, 79%).

EXAMPLE 2

2-(2-Acetoxyphenyl)-N-(1H-tetrazole-5-yl)-4-thiazolecarboxamide

To a suspension of 2-(2-acetoxyphenyl)-4-thiazolecarboxylic acid (600 mg) in dry benzene (12 ml) was added dropwise thionyl chloride (0.83 ml) under ice-cooling and the produced mixture was refluxed for 1 hour. The solvent was removed and the residue was treated with dry benzene (5 ml), which was then evaporated. The addition and evaporation of solvent was repeated using dry toluene (5 ml) to afford the acid chloride.

Then, 5-aminotetrazole (194 mg) was dissolved in tetrahydrofuran (80 ml) and triethylamine (0.32 ml) and to this solution was added dropwise a solution of the acid chloride above in tetrahydrofuran (5 ml) at room temperature. The reaction mixture was allowed to react under the same condition for 1.5 hours and concentrated. The residue was treated with water and acidified with 2N-HCl under ice-cooling. The produced solids were filtered, washed with water, dried and washed again with ether to give the desired 2-(2-acetoxyphenyl)-N-(1H-tetrazole-5-yl)-4-thiazolecarboxamide (627 mg, 83%).

EXAMPLE 3

2-(2-Methoxyphenyl)-N-(1H-tetrazole-5-yl)-4-thiazolecarboxamide sodium salt

To a suspension of 2-(2-methoxyphenyl)-N-(1H-tetrazole-5-yl)-4-thiazolecarboxamide (194 mg) in water (30 ml) was added 0.1N aqueous sodium hydroxide (6.41 ml) and the mixture was allowed to react at 85° C. for 1 hour. After removing the solvent, and the residue was crystallized by adding acetone. The produced solids were filtered and dried to give 2-(2-methoxyphenyl)-N-(1H-tetrazole-5-yl)-4-thiazolecarboxamide sodium salt (199 mg, 95%).

EXAMPLE 4

2-(2-Hydroxyphenyl)-N-(1H-tetrazole-5-yl)-4-thiazolecarboxamide 2-aminoethanol salt To a suspension of 2-(2-hydroxyphenyl)-N-(1H-tetrazole-5-yl)-4-thiazolecarboxamide (200 mg) in dry methanol (15 ml) was added 2-aminoethanol (0.045 ml) and allowed to dissolve. After allowing for additional 30 minutes at room temperature, the produced solids was filtered and washed with dry ether and then with dry acetone. The filtrate was concentrated and the residue was crystallized by adding dry ether. These crystals wrere combined and dried to give white solids of 2-(2-hydroxyphenyl)-N-(1H-tetrazole-5-yl)-4-thiazolecarboxamide 2-aminoethanol salt (130 mg, 54%).

EXAMPLE 5

2-(2-Aminophenyl)-N-(1H-tetrazole-5-yl)-4-thiazolecarboxamide

To a solution of 2-(2-nitrophenyl)-N-(1H-tetrazole-5-yl)-4-thiazolecarboxamide (200 mg) in a mixed solvent of dry tetrahydrofuran (THF, 30 ml) and dry DMF (13.7 ml) was added (10%) palladium on charcoal (200 mg) and the mixture was hydrogeneted for 22 hours. The catalyst was sucked off and the filtrate was concentrated under reduced pressure. The residue was treated with water (200 mg) to form crystals, which were filtered and dried to give colorless solids of 2-(2-aminophenyl)-N-(1H-tetrazole-5-yl)-4-thiazolecarboxamide (162 mg, 89%).

EXAMPLE 6

2-(3-Hydroxy-2-pyridyl)-N-(1H-tetrazole-5-yl)-4-thiazolecarboxamide

A suspension of 2-(3-hydroxy-2-pyridyl)-4-thiazolecarboxylic acid (200 mg) and N,N'-carbonyldiimidazole (hereinafter, referred to as CDI) (291.9 mg) in dry DMF (7 ml), prepared under argon atmosphere, was heated at 80° C. for 1.5 hours. A solution of 5-aminotetrazole (91.9 mg) in dry DMF (3 ml) was added dropwise thereto and allowed to react at 85° C. for 3.5 hours. Then the reaction mixture was cooled to room temperature. The produced solids were filtered with suction, washed with DMF and THF and dried to give white solids of 2-(3-hydroxy-2-pyridyl)-N-(1H-tetrazole-5-yl)-4-thiazolecarboxamide (140 mg, 54%), m.p. above 300° C.

EXAMPLE 7

2-(2-Furyl)-N-(1H-tetrazole-5-yl)-4-thiazolecarboxamide

A solution of 2-(2-furyl)-4-thiazolecarboxylic acid (300 mg) and CDI (373.8 mg) in a mixed solvent of dry DMF (10 mg) and dry DMSO (2 ml) was prepared at 100° C. and allowed to react under the same condition for 1 hour. Then a solution of 5-aminotetrazole (156.9 mg) in dry DMF (2 ml) was added dropwise thereto and the reaction was continued for additional 3 hours. The solvent was removed from the reaction mixture. The residue was treated with water and acidified with 2N-HCl. The produced solids were filtered, washed sufficiently with water and then with ether, and dried to give yellow ocher solids of 2-(2-furyl)-N-(1H-tetrazole-5-yl)-4-thiazolecarboxamide (174 mg, 43%), m.p. 275°–277° C.

EXAMPLE 8

2-(5-Methyl-2-thienyl)-5-methyl-N-(1H-tetrazole-5-yl)-4-thiazolecarboxamide

A solution of 2-(5-methyl-2-thienyl)-5-methyl-4-thiazolecarboxylic acid (300 mg) and CDI (304.9 mg) in dry DMF (3 ml) was allowed to react at room temperature for 1 hour. Then a solution of 5-aminotetrazole (128 mg) in dry DMF (2 ml) was added dropwise and the mixture was heated at 70° C. for 3 hours. The solvent was removed from the reaction mixture, and the residue was treated with water and acidified with 2N-HCl under ice-cooling. The produced solids were filtered with suction, washed sufficiently with water and dried to give pale yellow solids of 2-(5-methyl-2-thienyl)-5-methyl-N-(1H-tetrazole-5-yl)-4-thiazolecarboxamide (372.9 mg, 97%), m.p. 278°–280° C. (from methanol-THF-water).

EXAMPLE 9

2-(3-Hydroxy-2-pyridyl)-N-(1H-tetrazole-5-yl)-4-thiazolecarboxamide monosodium salt To a suspension of 2-(3-hydroxy-2-pyridyl)-N-(1H-tetrazole-5-yl)-4-thiazolecarboxamide (260 mg) in water (10 ml) was added 1N aqueous sodium hydroxide (0.899 ml) and the mixture was heated at 80° C. for 30 minutes. Then the solvent was removed from the reaction mixture and the residue was crystallized from acetone. The produced crystals were filtered by suction and dried to give yellow solids of 2-(3-hydroxy-2-pyridyl)-N-(1H-tetrazole-5-yl)-4-thiazolecarboxamide monosodium salt (269 mg, 96%), m.p. above 300° C.

EXAMPLE 10

2-(2-Furyl)-N-(1H-tetrazole-5-yl)-4-thiazolecarboxamide 2-aminoethanol salt

To a suspension of 2-(2-furyl)-N-(1H-tetrazole-5-yl)-4-thiazolecarboxamide (100 mg) in dry methanol (10 ml) was added 2-aminoethanol (0.025 ml) and allowed to react, after dissolving, at room temperature for 30 minutes. Then the solvent was removed from the reaction mixture and the residue was crystallized by triturating with dry ether. The produced crystals were filtered with suction and dried to give yellow solids of 2-(2-furyl)-N-(1H-tetrazole-5-yl)-4-thiazolecarboxamide 2-aminoethanol salt (100.3 mg, 81%), m.p. 255°–260° C.

The following compounds of the formula (I) were prepared according to the processes described in the above EXAMPLES 1-2 or 6-8.

2-(2-hydroxyphenyl)-N-(1H-tetrazole-5-yl)-4-thiazolecarboxamide (I-1) from 2-(2-hydroxyphenyl)-4-thiazolecarboxylic acid 2-(3-methoxyphenyl)-N-(1H-tetrazole-5-yl)-4-thiazolecarboxamide (I-3) from 2-(3-methoxyphenyl)-4-thiazolecarboxylic acid 2-(4-methoxyphenyl)-N-(1H-tetrazole-5-yl)-4-thiazolecarboxamide (I-4) from 2-(4-methoxyphenyl)-4-thiazolecarboxylic acid 2-(2-methylphenyl)-N-(1H-tetrazole-5-yl)-4-thiazolecarboxamide (I-5) from 2-(2-methylphenyl)-4-thiazolecarboxylic acid 2-(3-methylphenyl)-N-(1H-tetrazole-5-yl)-4-thiazolecarboxamide (I-6) from 2-(3-methylphenyl)-4-thiazolecarboxylic acid 2-(4-methylphenyl)-N-(1H-tetrazole-5-yl)-4-thiazolecarboxamide (I-7) from 2-(4-methylphenyl)-4-thiazolecarboxylic acid 2-(4-isopropylphenyl)-N-(1H-tetrazole-5-yl)-4-thiazolecarboxamide (I-8) from 2-(4-isopropylphenyl)-4-thiazolecarboxylic acid 2-[(t-butyl)phenyl]-N-(1H-tetrazole-5-yl)-4-thiazolecarboxamide (I-9) from 2-[4-(t-butyl)phenyl]-4-thiazolecarboxylic acid 2-(4-chlorophenyl)-N-(1H-tetrazole-5-yl)-4-thiazolecarboxamide (I-10) from 2-(4-chlorophenyl)-4-thiazolecarboxylic acid 2-(2-nitrophenyl)-N-(1H-tetrazole-5-yl)-4-thiazolecarboxamide (I-11) from 2-(2-nitrophenyl)-4-thiazolecarboxylic acid 2-(3,4,5-trimethoxyphenyl)-N-(1H-tetrazole-5-yl)-4-thiazolecarboxamide (I-12) from 2-(3,4,5-trimethoxyphenyl)-4-thiazolecarboxylic acid 2-(3,5-dimethoxyphenyl)-N-(1H-tetrazole-5-yl)-4-thiazolecarboxamide (I-13) from 2-(3,5-dimethoxyphenyl)-4-thiazolecarboxylic acid 2-(2,4-dimethoxyphenyl)-N-(1H-tetrazole-5-yl)-4-thiazolecarboxamide (I-14) from 2-(2,4-dimethoxyphenyl)-4-thiazolecarboxylic acid 2-(phenyl)-N-(1H-tetrazole-5-yl)-4-thiazolecarboxamide (I-15) from 2-(phenyl)-4-thiazolecarboxylic acid 2-(4-hydroxyphenyl)-N-(1H-tetrazole-5-yl)-4-thiazolecarboxamide (I-16) from 2-(4-hydroxyphenyl)-4-thiazolecarboxylic acid 2-(3-trifluoromethylphenyl)-N-(1H-tetrazole-5-yl)-4-thiazolecarboxamide (I-17) from 2-(3-trifluoromethylphenyl)-4-thiazolecarboxylic acid 2-(3-hydroxy-2-naphthyl)-N-(1H-tetrazole-5-yl)-4-thiazolecarboxamide (I-18) from 2-(3-hydroxy-2-naphthyl)-4-thiazolecarboxylic acid 2-(5-chloro-2-hydroxyphenyl)-N-(1H-tetrazole-5-yl)-4-thiazolecarboxamide (I-19) from 2-(5-chloro-2-hydroxyphenyl)-4-thiazolecarboxylic acid 2-(2-hydroxy-5-methoxyphenyl)-N-(1H-tetrazole-5-yl)-4-thiazolecarboxamide (I-20) from 2-(2-hydroxy-5-methoxyphenyl)-4-thiazolecarboxylic acid 2-(2-hydroxy-5-nitrophenyl)-N-(1H-tetrazole-5-yl)-4-thiazolecarboxamide (I-21) from 2-(2-hydroxy-5-nitrophenyl)-4-thiazolecarboxylic acid 2-(2-hydroxy-5-methylphenyl)-N-(1H-tetrazole-5-yl)-4-thiazolecarboxamide (I-22) from 2-(2-hydroxy-5-methylphenyl)-4-thiazolecarboxylic acid 2-(2-benzyloxyphenyl)-N-(1H-tetrazole-5-yl)-4-thiazolecarboxamide (I-23) from 2-(2-benzyloxyphenyl)-4-thiazolecarboxylic acid 2-(2-stearyloxyphenyl)-N-(1H-tetrazole-5-yl)-4-thiazolecarboxamide (I-25) from 2-(2-stearyloxyphenyl)-4-thiazolecarboxylic acid 2-(methyl)-N-(1H-tetrazole-5-yl)-4-thiazolecarboxamide (I-26) from 2-(methyl)-4-thiazolecarboxylic acid 2-(4-methylphenyl)-5-methyl-N-(1H-tetrazole-5-yl)-4-thiazolecarboxamide (I-27) from 2-(4-methylphenyl)-5-methyl-4-thiazolecarboxylic acid 2-(4-methylphenyl)-5-isopropyl-N-(1H-tetrazole-5-yl)-4-thiazolecarboxamide (I-28) from 2-(4-methylphenyl)-5-isopropyl-4-thiazolecarboxylic acid 2-(4-methoxyphenyl)-5-methyl-N-(1H-tetrazole-5-yl)-4-thiazolecarboxamide (I-29) from 2-(4-methoxyphenyl)-5-methyl-4-thiazolecarboxylic acid 2-(2-pyridyl)-N-(1H-tetrazole-5-yl)-4-thiazolecarboxamide (I-32) from 2-(2-pyridyl)-4-thiazolecarboxylic acid 2-(3-pyridyl)-N-(1H-tetrazole-5-yl)-4-thiazolecarboxamide (I-33) from 2-(3-pyridyl)-4-thiazolecarboxylic acid 2-(4-pyridyl)-N-(1H-tetrazole-5-yl)-4-thiazolecarboxamide (I-34) from 2-(4-pyridyl)-4-thiazolecarboxylic acid 2-(6-methyl-2-pyridyl)-N-(1H-tetrazole-5-yl)-4-thiazolecarboxamide (I-35) from 2-(6-methyl-2-pyridyl)-4-thiazolecarboxylic acid 2-(5-bromo-3-pyridyl)-N-(1H-tetrazole-5-yl)-4-thiazolecarboxamide (I-36) from 2-(5-bromo-3-pyridyl)-4-thiazolecarboxylic acid 2-(2-pyrazinyl)-N-(1H-tetrazole-5-yl)-4-thiazolecarboxamide (I-37) from 2-(2-pyrazinyl)-4-thiazolecarboxylic acid 2-(2-quinolyl)-N-(1H-tetrazole-5-yl)-4-thiazolecarboxamide (I-38) from 2-(2-quinolyl)-4-thiazolecarboxylic acid 2-(2-thienyl)-N-(1H-tetrazole-5-yl)-4-thiazolecarboxamide (I-40) from 2-(2-thienyl)-4-thiazolecarboxylic acid 2-(2-furyl)-5-methyl-N-(1H-tetrazole-5-yl)-4-thiazolecarboxamide (I-41) from 2-(2-furyl)-5-methyl-4-thiazolecarboxylic acid Also, the following salts were prepared according to the processes described in EXAMPLES 9 and 10.

2-(2-hydroxyphenyl)-N-(1H-tetrazole-5-yl)-4-thiazolecarboxamide-sodium salt (I-1')

2-(2-hydroxyphenyl)-N-(1H-tetrazole-5-yl)-4-thiazolecarboxamide-2-aminoethanol salt (I-1'')

2-(4-methoxyphenyl)-N-(1H-tetrazole-5-yl)-4-thiazolecarboxamide-2-aminoethanol salt (I-4')

2-(4-methylphenyl)-N-(1H-tetrazole-5-yl)-4-thiazolecarboxamide-2-aminoethanol salt (I-7')

2-(6-methyl-2-pyridyl)-N-(1H-tetrazole-5-yl)-4-thiazolecarboxamide-2-aminoethanol salt (I-35')

2-(2-pyrazinyl)-N-(1H-tetrazole-5-yl)-4-thiazolecarboxamide-2-aminoethanol salt (I-37')

2-(2-thienyl)-N-(1H-tetrazole-5-yl)-4-thiazolecarboxamide-2-aminoethanol salt (I-40')

Compounds of the formulas (I) and (II) and salts thereof prepared according to the above Preparations and EXAMPLES are shown in Tables 1 and 2, in which melting points show those after recrystallization from MeOH, MeOH-THF-H$_2$O, DMF-H$_2$O or THF-H$_2$O in the case of free carboxylic acids, or from Et$_2$O-EtOH in the case of salts.

| FORMULATION 1 | |
|---|---|
| (1) Active ingredient | 25.00 mg |
| (2) Lactose | 49.00 mg |
|     Crystalline cellulose | 36.00 mg |
|     Corn starch | 5.00 mg |
| (3) Hydroxypropyl cellulose | 1.00 mg |
| (4) ECG505 (carboxymethyl cellulose calcium) | 2.00 mg |
| (5) Magnesium stearate | 1.00 mg |
| (6) Talc | 1.00 mg |
| Total | 120 mg |

(1)+(2) were kneaded with 5% aqueous solution of (3), dried, and granulated, to which (4), (5), and (6) were added to mix together. The mixture was pressed into tablets of 120 mg each, 7 mm in diameter.

| FORMULATION 2 | |
|---|---|
| (1) Active ingredient | 50.00 mg |
| (2) Lactose | 124.50 mg |
| (3) Corn starch | 20.00 mg |
| (4) Hydroxypropyl cellulose | 2.00 mg |
| (5) Light anhydrous silicic acid | 1.50 mg |
| (6) Magnesium stearate | 2.00 mg |
| Total | 200 mg |

(1)+(2)+(3) were kneaded with 5% aqueous solution of (4), dried, and granulated, to which (5) and (6) were added to mix together, and the mixture was filled in hard gelatine capsule.

(In the above FORMULATIONS 1 and 2, the term active ingredient means optional one of the compounds of the formula (I)).

TEST EXAMPLE 1

Anti-passive cutaneous anaphylaxis (PCA) activity in rats (Materials and Method)

(1) Animals used

Wistar strain male rats (6 weeks old) were purchased from Shizuoka Experimental Animal Agricultural Cooperative (Japan), habituated to a breeding environment for 1 week before using for the experiment.

(2) Preparation of antiserum

Preparation of antiserum was carried out according to the method described in J. Immunol. 106, 1002–1011 (1971).

Thus, Ascaris suum extract was dinitrophenylated (DNP-As) and infused subcutaneously together with dead Bordetella pertussis at four sites on the foot-pad. After 5 days, the rats were boostered with DNP-As (1 mg) at the dosal muscle. After 3 days, bloods samples were collected and serum was separated which was used as anti DNP-As antiserum. The titer of the antiserum was measured by rats 48-hours PCA and found to be 1:200.

(3) 48-Hours PCA

Rats were sensitized with 35 times dilution of anti DNP-As antiserum administered at two sites in the pre-clipped right dosal skin. After 48 hours, DNP-As (500 μg in 0.5% Evans blue-physiological saline (1 ml) was administered into caudal vein to elicit the reaction. Then, 30 minutes later, the animals were decapitated, the dosal skin was peeled, two sensitized areas as well as one control area were cut off and analyzed for Evans blue exudation which was used as an indicative of the reaction according to the method disclosed in Microbiol. Immunol. 22, 89–101 (1978). Thus, cut skins were treated with 1N-NaOH (1 ml) and incubated at 37° C. for 16 hours to dissolve the skin tissue. A mixed solution (9 ml) of 0.6N-phosphoric acid-acetone (5:13) was added and the mixture was centrifuged (300 r.p.m) for 15 minutes. The supernatant was assayed for absorption at 620 nm and the exudation of Evans blue was determined. Test compounds (I) were administered either into caudal vein 5 minutes before the elicitation of the reaction, or perorally as a suspension in 0.5% 1 hour before the elicitation.

(Results)

The obtained results are shown in the following Tables from which it can be clearly seen that the compounds of the invention inhibit significantly the reaction and hence have a potent anti-PCA activity.

| Compound No. | I.V. (candal vein) Dose (mg/kg) | Inhibition (%) |
| --- | --- | --- |
| I-1 | 2 | 99 |
| I-1' | 0.5 | 67 |
|  | 1.5 | 98 |
|  | 5 | 98 |
| I-2 | 2 | 99 |
| I-3 | 2 | 99 |
| I-4 | 2 | 98 |
| I-17 | 2 | 98 |
| I-19 | 2 | 97 |
| I-20 | 2 | 93 |
| I-21 | 2 | 98 |
| I-22 | 2 | 81 |
| I-23 | 2 | 98 |
| DSCG | 5 | 92 |

| Compound No. | P.O Dose (mg/kg) | Inhibition (%) |
| --- | --- | --- |
| I-1 | 50 | 40 |
| I-1" | 50 | 78 |
| I-2" | 50 | 60 |
| I-3' | 30 | 77 |
| I-7 | 30 | 76 |
| I-7' | 30 | 69 |
| I-27 | 25 | 91 |
| Tranilast | 50 | 0 |

TEXT EXAMPLE 2

Anti-passive cutaneous anaphylaxis (PCA) activity in rats (Materials and Method)

The same as those in TEST EXAMPLE 1 except that the compounds (I) were administered only by P.O.

(Results)

The following results show that the compounds of the invention inhibit significantly the reaction and hence have a potent anti-PCA activity.

| Compound No. | Dose (mg/kg) | Inhibition (%) |
| --- | --- | --- |
| I-35 | 25 | 50 |
| I-37' | 25 | 55 |
| I-39' | 25 | 75 |
| I-40' | 25 | 80 |
| I-42 | 25 | 73 |
| Tranilast | 50 | 0 |

TEST EXAMPLE 3

In the tests reported in the above TEST EXAMPLES 1 and 2, no toxic effects were observed.

TABLE 1

| Compound No. | A | R | m.p. (°C.) | IR (KBr, cm$^{-1}$) |
| --- | --- | --- | --- | --- |
| II-1 | 2-hydroxyphenyl | H | 268–269 | 3200–2100 1670 |
| II-2 | 2-methoxyphenyl | H | 182–184 | 3200–2100 1680 |
| II-3 | 3-methoxyphenyl | H | 132–133 | 3200–2100 1700 |
| II-4 | 4-methoxyphenyl | H | 173–176 | 3250–2100 1720 |
| II-5 | 2-methylphenyl | H | 122–123 | 3300–2000 1700 |
| II-6 | 3-methylphenyl | H | 150–154 | 3300–2000 1680 |
| II-7 | 4-methylphenyl | H | 172–174 | 3100–2150 1680 |
| II-8 | 4-isopropylphenyl | H | 164–166 | 3200–2000 1680 |

TABLE 1-continued

| Compound No. | A | R | m.p. (°C.) | IR (KBr, cm$^{-1}$) |
|---|---|---|---|---|
| II-9 | 4-(t-butyl)phenyl | H | 195–197 | 3200–2100 1690 |
| II-10 | 4-chlorophenyl | H | 188–189 | 3200–2300 1680 |
| II-11 | 2-nitrophenyl | H | 229–230 | 3100–2300 1710 |
| II-12 | 3,4,5-trimethoxyphenyl | H | 154–155 | 3600–2300 1720 |
| II-13 | 3,5-dimethoxyphenyl | H | 155–158 | 3150–2150 1680 |
| II-14 | 2,4-dimethoxyphenyl | H | 240–242 | 3300–2000 1710 |
| II-15 | phenyl | H | 172–175 | 3200–2100 1690 |
| II-16 | 4-hydroxyphenyl | H | 218–221 | 3500–2300 1730 |
| II-17 | 3-trifluoromethylphenyl | H | 200–202 | 3100–2050 1720 |
| II-18 | 3-hydroxy-2-naphthyl | H | 295–298 | 3700–2100 1690 |
| II-19 | 5-chloro-2-hydroxyphenyl | H | above 300° C. | 3450 3300–2100 1690 |
| II-20 | 2-hydroxy-5-methoxyphenyl | H | 263–265 | 3150–2100 1690 |
| II-21 | 2-hydroxy-5-nitrophenyl | H | 276–278 | 3300–2000 1720 |
| II-22 | 2-hydroxy-5-methylphenyl | H | 272–275 | 3400, 1690 |
| II-23 | 2-benzyloxyphenyl | H | 179–181 | 3250–2100 1700 |
| II-24 | 2-acetoxyphenyl | H | 189–191 | 3200–2300 1760, 1710 |
| II-25 | 2-stearyloxyphenyl | H | 89–92 | 2900–2850 1680 |
| II-26 | methyl | H | 144–147 | 3500 3400–2100 1670 |
| II-27 | 4-methylphenyl | methyl | 199–200 | 3300–2000 1670 |
| II-28 | 4-methylphenyl | isopropyl | 114–116 | 1680 3300 |
| II-29 | 4-methoxypheny | methyl | 166–168 | 3200–2100 1680 |
| II-30 | 2-aminophenyl | H | | |
| II-31 | 3-hydroxy-2-pyridyl | H | above 300° C. | 3700–2000 1700, 1660 |
| II-32 | 2-pyridyl | H | 270–274 | 3600–2000 1710 |
| II-33 | 3-pyridyl | H | 265–268 | 3100–1720 |
| II-34 | 4-pyridyl | H | 282–290 | 2350, 1720 1600 |
| II-35 | 6-methyl-2-pyridyl | H | above 300° C. | 3700–2800 |
| II-36 | 5-bromo-3-pyridyl | H | 266–268 | 3070, 1690 |
| II-37 | 2-pyrazinyl | H | 248–249 | 3200–2100 1720 |
| II-38 | 2-quinolyl | H | 267–270 | 3300–2100 1690, 1600 |
| II-39 | 2-furyl | H | 257–265 | 3700–3200 3100, 1750 1600 |
| II-40 | 2-thienyl | H | 161–162 | 3300–2100 1690 |
| II-41 | 2-furyl | methyl | 174–175 | 3500–2000 1680 |
| II-42 | 5-methyl-2-thienyl | methyl | 160–161 | 1670 1680, 1600 |

TABLE 2

| Compound No. | A | R | Ex. No. | Yield (%) | m.p. (°C.) | MS (m/z) | IR (KBr, cm$^{-1}$) |
|---|---|---|---|---|---|---|---|
| I-1 | 2-hydroxyphenyl | H | 1 | 90 | 282–285 | 288(M$^+$) 204(BP) | 3450, 3300–2500 1690, 1600 |
| I-1' | 2-hydroxyphenyl (sodium salt) | H | 3 | 90 | above 300° C. | | 3700–2000 3100, 1650 |

TABLE 2-continued

| Compound No. | A | R | Ex. No. | Yield (%) | m.p. (°C.) | MS (m/z) | IR (KBr, cm$^{-1}$) |
|---|---|---|---|---|---|---|---|
| I-1″ | 2-hydroxyphenyl (2-aminoethanol salt) | H | 4 | 54 | 288–291 | | 3700–2000 1690 |
| I-2 | 2-methoxyphenyl | H | 1 | 79 | 284–286 | 302(M$^+$) 191(BP) | 3250, 3100 1700 |
| I-2′ | 2-methoxyphenyl (sodium salt) | H | 3 | 95 | 272–274 | | 3700–2800 1640 |
| I-2″ | 2-methoxyphenyl (2-aminoethanol salt) | H | 4 | 80 | 275–278 | | 3700–1900 1670 |
| I-3 | 3-methoxyphenyl | H | 1 | 87 | 273–275 | 302(M$^+$) 218(BP) | 3200, 3000 1690 |
| I-4 | 4-methoxyphenyl | H | 1 | 57 | 282–283 | 302(M$^+$) 218(BP) | 3250, 3150–2000 1690 |
| I-4′ | 4-methoxyphenyl (2-aminoethanol salt) | H | 4 | 81 | 294–298 | | 3700–2100 1680 |
| I-5 | 2-methylphenyl | H | 1 | 73 | 263–265 | 286(M$^+$) 202(BP) | 3300–3200 3100–2100 1690 |
| I-6 | 3-methylphenyl | H | 1 | 80 | 289–291 | 286(M$^+$) 202(BP) | 3200 3100–2200 1660 |
| I-7 | 4-methylphenyl | H | 1 | 79 | 289–279 | 286(M$^+$) 202(BP) | 3250, 3150–2100 1690 |
| I-7′ | 4-methylphenyl (2-aminoethanol salt) | H | 4 | 78 | 278–281 | | 3700–2200 1680 1560 |
| I-8 | 4-isopropylphenyl- | H | 1 | 77 | 258–261 | 314(M$^+$) 230(BP) | 3250 3150–2100 1690 |
| I-9 | 4-(t-butyl)phenyl | H | 1 | 65 | 278–279 | 328(M$^+$) 244(BP) | 3250 3150–2100 1680 |
| I-10 | 4-chlorophenyl | H | 1 | 85 | 297–298 | 306(M$^+$) 195(BP) | 3200, 3100 1690 |
| I-11 | 2-nitrophenyl | H | 1 | 69 | 270–273 | 317(M$^+$) 104(BP) | 3200, 3100 1700 |
| I-12 | 3,4,5-trimethoxyphenyl | H | 1 | 66 | 293–294 | 362 (M$^+$, BP) | 3300, 3150 1700 |
| I-13 | 3,5-dimethoxyphenyl | H | 1 | 82 | 265–267 | 332(M$^+$) 248(BP) | 3250, 3150–2100 1690 |
| I-14 | 2,4-dimethoxyphenyl | H | 1 | 88 | 288–291 | 332(M$^+$) 248(BP) | 3250, 1690 |
| I-15 | phenyl | H | 1 | 90 | 272–275 | 272(M$^+$) 161(BP) | 3250, 3150–2000 1680 |
| I-16 | 4-hydroxyphenyl | H | 1 | 96 | 289–292 | 288(M$^+$) 204(BP) | 3200–2300 1690, 1660 |
| I-17 | 3-trifluoromethylphenyl | H | 1 | 96 | 274–276 | 340(M$^+$) 57(BP) | 3200, 3100–2000 1660 |
| I-18 | 3-hydroxy-2-naphthyl | H | 1 | 47 | 288–290 | 338(M$^+$) 254(BP) | 3700, 2300 1680 |
| I-19 | 5-chloro-2-hydroxyphenyl | H | 1 | 72 | 291–293 | 322(M$^+$) 238(BP) | 3250, 1680 1050 |
| I-20 | 2-hydroxy-5-methoxyphenyl | H | 1 | 75 | 283–285 | 318(M$^+$) 234(BP) | 3600–2500 1670 |
| I-21 | 2-hydroxy-5-nitrophenyl | H | 1 | 75 | 290–291 | 338(M$^+$) 249(BP) | 3700–2000 1690 |
| I-22 | 2-hydroxy-5-methylphenyl | H | 1 | 76 | 278–280 | 302(M$^+$) 218(BP) | 1680, 1045 |
| I-23 | 2-benzyloxyphenyl | H | 1 | 84 | 282–283 | 378(M$^+$) 91(BP) | 3250, 3150–2150 1690, 1050 |
| I-24 | 2-acetoxyphenyl- | H | 2 | 83 | 234–236 | 330(M$^+$) 204(BP) | 3600–2300 3200, 1760 1790 |
| I-25 | 2-stearyloxyphenyl | H | 1 | 93 | 199–201 | 540(M$^+$) 204(BP) | 3250, 2900 2850, 1690 |
| I-26 | methyl | H | 1 | 89 | 250–251 | 211 [(M + 1)$^+$] 99(BP) | 3200, 1680 |
| I-27 | 4-methylphenyl | methyl | 1 | 81 | 265–268 | 300(M$^+$) 135(BP) | 3250, 1680 |
| I-28 | 4-methylphenyl | isopropyl | 1 | 65 | 254–256 | 328(M$^+$) 135(BP) | 3300 3100–2000 |

TABLE 2-continued

| Compound No. | A | R | Ex. No. | Yield (%) | m.p. (°C.) | MS (m/z) | IR (KBr, cm⁻¹) |
|---|---|---|---|---|---|---|---|
| I-29 | 4-methoxyphenyl | methyl | 1 | 60 | 272–273 | 316(M⁺) 151(BP) | 1690 3250, 3150–2200 |
| I-30 | 2-aminophenyl | H | 5 | 89 | 274–277 | 287(M⁺) 203(BP) | 1690 3500, 3350 3250, 1690 |
| I-31 | 3-hydroxy-2-pyridyl | H | 6 | 54 | above 300° C. | 289(M⁺) 205(BP) | 3700–2000 1660 |
| I-31' | 3-hydroxy-2-pyridyl (sodium salt) | H | 9 | 96 | above 300° C. | | 3700–2500 1680 |
| I-32 | 2-pyridyl | H | 6 | 31 | 274–277 | 273(M⁺) 78(BP) | 3400–2000 1660 |
| I-33 | 3-pyridyl | H | 6 | 50 | 276–278 | 273(M⁺) 162(BP) | 3700–2100 1690 |
| I-34 | 4-pyridyl | H | 6 | 54 | 289–292 | 273(M⁺) 162(BP) | 3200–2300 1680 |
| I-35 | 6-methyl-2-pyridyl | H | 6 | 51 | 291–293 | 287(M⁺) 231(BP) | 3300–2500 1660 |
| I-35' | 6-methyl-2-pyridyl (2-aminoethanol salt) | H | 10 | 97 | 281–284 | | 3700–2000 1680 |
| I-36 | 5-bromo-3-pyridyl | H | 6 | 35 | above 300° C. | 353(M⁺) 57(BP) | 1660 1580 |
| I-37 | 2-pyrazinyl | H | 6 | 87 | above 300° C. | 274(M⁺) 163(BP) | 3300–2200 1670 1600 |
| I-37' | 2-pyrazinyl (2-aminoethanol salt) | H | 10 | 80 | above 300° C. | | 3700–2000 1680 1560 |
| I-38 | 2-quinolyl | H | 6 | 86 | above 300° C. | 323(M⁺) 128(BP) | 3250, 3100 1690 1580 |
| I-39 | 2-furyl | H | 7 | 43 | 275–277 | 262(M⁺) 178(BP) | 3350–2100 1670 1600 |
| I-39' | 2-furyl (2-aminoethanol salt) | H | 10 | 81 | 255–260 | | 3700–2200 1660 1600 |
| I-40 | 2-thienyl | H | 7 | 76 | 271–276 | 278(M⁺) 194(BP) | 3250 3100–2100 1680, 1610 |
| I-40' | 2-thienyl (2-aminoethanol salt) | H | 10 | 70 | 260–264 | | 3700–2100 1670 1660 |
| I-41 | 2-furyl | methyl | 8 | 74 | 267–270 | 276(M⁺) 192(BP) | 3250 3150–2200 1680, 1620 |
| I-42 | 5-methyl-2-thienyl | methyl | 8 | 97 | 278–280 | 306(M⁺) 141(BP) | 3300, 3250 3100–2200 1680, 1600 |

| Compound No. | ¹H—NMR(DMSO—d₆) δ |
|---|---|
| I-1 | 12.42(1H,br-s,—CON$\underline{H}$), 8.57(1H,s,thiazole), 8.82–8.35(1H,m,Ar—$\underline{H}$), 7.65–6.78(3H,m,Ar—$\underline{H}$) |
| I-1' | 8.43–8.26(1H,m,Ar—$\underline{H}$) 8.30(1H,s,thiazole) 7.23–6.73(3H,m,Ar—$\underline{H}$) |
| I-2 | 12.33(1H,br-s,—CON$\underline{H}$), 8.63(1H,s,thiazole), 8.83–8.63(1H,m,Ar—$\underline{H}$), 7.73–6.97(3H,m,Ar—$\underline{H}$) 4.07(3H,s,—OCH₃) |
| I-3 | 12.27(1H,br-s,—CON$\underline{H}$), 8.60(1H,s,thiazole), 7.83–6.97(4H,m,Ar—$\underline{H}$), 3.87(3H,s,—OCH₃) |
| I-4 | 12.20(1H,br-s,—CON$\underline{H}$), 8.50(1H,s,thiazole), 8.07,7.03(4H,AB—q,Ar—$\underline{H}$), 3.83(3H,s,—CH₃) |
| I-7 | 12.30(1H,br-s,—CON$\underline{H}$), 8.60(1H,s,thiazole), 8.00,7.27(4H,AB—q,Ar—$\underline{H}$), 2.43(3H,s,—CH₃) |
| I-10 | 12.37(1H,br-s,—CON$\underline{H}$) 8.67(1H,s,thiazole) 8.20,7.53(4H,AB—q,Ar—$\underline{H}$) |
| I-11 | 12.17(1H,br-s,—CON$\underline{H}$) 8.80(1H,s,thiazole) 8.10–7.67(4H,m,Ar—$\underline{H}$) |
| I-12 | 12.10(1H,br-s,—CON$\underline{H}$) 8.60(1H,s,thiazole) 7.40(2H,s,Ar—$\underline{H}$), 3.93(6H,s,—OCH₃X2), 3.73(3H,s,—OCH₃) |

-continued

| Compound No. | $^1$H—NMR(DMSO—$d_6$) δ |
|---|---|
| I-13 | 12.20(1H,br-s,—CON$\underline{H}$), 8.57(1H,s,thiazole), 7.40–6.50(3H,m,Ar—$\underline{H}$), 3.83(6H,s,—OC$\underline{H_3}$X2) |
| I-15 | 12.27(1H,br-s,—CON$\underline{H}$) 8.63(1H,s,thiazole) 8.33–7.33(5H,m,Ar—$\underline{H}$) |
| I-16 | 12.20(1H,br-s,—CON$\underline{H}$) 8.47(1H,s,thiazole) 7.93,6.87(4H,AB—q,Ar—$\underline{H}$) |
| I-17 | 12.40(1H,br-s,—CON$\underline{H}$) 8.70(1H,s,thiazole) 8.63–7.60(4H,m,Ar—$\underline{H}$) |
| I-18 | 12.43(1H,br-s,—CON$\underline{H}$), 9.13(1H,s,naphthalene), 8.67(1H,s,thiazole), 8.17–7.13(5H,m,naphthalene) |
| I-19 | 12.47(1H,br-s,—CON$\underline{H}$), 8.55(1H,s,thiazole), 8.78–8.55(1H,m,Ar—$\underline{H}$), 8.07–6.92(2H,m,Ar—$\underline{H}$) |
| I-20 | 12.33(1H,br-s,—CON$\underline{H}$) 10.47(1H,br-s,—O$\underline{H}$ or —N$\underline{H}$) 8.60(1H,s,thiazole) 8.10–6.97(3H,m,Ar—$\underline{H}$), 3.83(3H,s,—OC$\underline{H_3}$), |
| I-21 | 12.58(1H,br-s,—CON$\underline{H}$), 9.38(1H,d,Ar—$\underline{H}$), 8.70(1H,s,thiazole) 8.38–8.05(1H,m,Ar—$\underline{H}$) 7.17(1H,d,Ar—$\underline{H}$) |
| I-22 | 12.38(1H,br-s,—CON$\underline{H}$) 11.00(1H,br-s,—O$\underline{H}$ or —N$\underline{H}$) 8.61(1H,s,thiazole) 8.26–7.18(2H,m,Ar—$\underline{H}$), 6.96(1Hd,Ar—$\underline{H}$),2.35(3H,s,—C$\underline{H_3}$) |
| I-23 | 12.57–12.20(1H,br-s,—CON$\underline{H}$) 8.90–8.47(1H,m,Ar—$\underline{H}$), 8.57(1H,s,thiazole), 7.73–6.90(8H,m,Ar—$\underline{H}$), 5.40(2H,s,—OC$\underline{H_2}$—Ph) |
| I-24 | 12.43(1H,br-s,—CON$\underline{H}$), 8.70(1H,s,thiazole) 8.63–7.20(4H,m,Ar—$\underline{H}$), 2.50(3H,s,—COC$\underline{H_3}$) |
| I-25 | 0.60–1.03(3H,m,—C$\underline{H_3}$), 1.03–2.16(32H,m,C$\underline{H_2}$), 3.93–4.33(2H,m,—OC$\underline{H_2}$—), 8.50(1H,s,thiazole), 6.87–8.87(4H,m,Ar—$\underline{H}$) (DMSO—$d_6$ + CDCl$_3$) |
| I-26 | 2.77(3H,s,—C$\underline{H_3}$) 8.47(1H,s,thiazole) 12.03(1H,brs,—CON$\underline{H}$—) |
| I-27 | 2.38(3H,s,C$\underline{H_3}$—Ph), 2.87(3H,s,thiazole methyl), 7.28(2H,d,Ar—$\underline{H}$) 7.98(2H,d,Ar—$\underline{H}$), 12.10(1H,brs,—CON$\underline{H}$—) |
| I-29 | 2.82(3H,s,thiazole methyl), 3.83(3H,s,C$\underline{H_3}$O—ph), 6.98(2H,d,Ar—H), 7.98(2H,d,Ar—H), 12.02(1H,brs,—CON$\underline{H}$—) |
| I-30 | 12.63(1H,br-s,—CON$\underline{H}$) 8.53(1H,s,thiazole) 7.63–6.47(4H,m,Ar—$\underline{H}$) |

-continued

| Compound No. | $^1$H—NMR(DMSO—$d_6$) δ |
|---|---|
| I-32 | 7.37–8.83(5H,m,Ar—$\underline{H}$, thiazole $\underline{H}$), 12.33(1H,brs,—CON$\underline{H}$—) |
| I-35 | 2.57(3H,s,—C$\underline{H_3}$), 7.23–8.43(3H,m,Ar—$\underline{H}$), 8.70(1H,s,thiazole $\underline{H}$), 12.37(1H,brs,—CON$\underline{H}$—) |
| I-37 | 8.57–9.00 (3H,m,pyrazinyl-5-$\underline{H}$, -6-$\underline{H}$, thiazole $\underline{H}$), 9.65(1H,d,pyrazinyl-3-$\underline{H}$), 12.37(1H,brs,—CON$\underline{H}$—) |
| I-38 | 7.37–8.67(6H,m,Ar—$\underline{H}$), 8.75(1H,s,thiazole $\underline{H}$), 12.47(1H,brs,—CON$\underline{H}$—) |
| I-39 | 6.72(1H,dd,furyl-4-$\underline{H}$), 7.25(1H,d,furyl-3-$\underline{H}$), 7.92(1H,d,furyl-5-$\underline{H}$), 8.60(1H,s,thiazole $\underline{H}$), 12.25(1H,brs,—CON$\underline{H}$—) |
| I-40 | 7.18(1H,t,thienyl-4-$\underline{H}$), 7.78(2H,d,thienyl-3-$\underline{H}$-5-$\underline{H}$), 8.58(1H,s,thiazole $\underline{H}$), 12.23(1H,brs,—CON$\underline{H}$—) |
| I-41 | 2.82(3H,s,thiazole methyl), 6.67(1H,dd,furyl-4-$\underline{H}$), 7.22(1H,d,furyl-3-$\underline{H}$), 7.83(1H,d,furyl-5-$\underline{H}$), 11.90(1H,brs,—CON$\underline{H}$—) |
| I-42 | 2.53(3H,s,thienyl methyl), 2.82(3H,s,thiazole methyl), 6.73–7.07(1H,m,thienyl-4-$\underline{H}$), 7.55(1H,d,thienyl-3-$\underline{H}$), 11.73(1H,brs,—CON$\underline{H}$—) |

What is claimed is:

1. A compound of the formula:

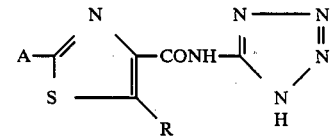

wherein

A is $C_1$–$C_6$ alkyl group; an aryl group which is unsubstituted or substituted with at least one substituent selected from hydroxy, alkoxy, aryl-($C_1$–$C_6$) alkoxy, $C_1$–$C_6$ alkylcarbonyloxy, halo-($C_1$–$C_6$) alkyl, halogen, nitro and amino; a 5- or 6-membered heterocyclic group containing one or two ring hetero atoms selected from the group consisting of oxygen, nitrogen and sulfur; or a condensed heterocyclic group as defined above and a benzene nucleus, the heterocyclic group and the condensed heterocyclic group being unsubstituted or substituted with at least one substituent selected from hydroxy, $C_1$–$C_6$ alkyl and halogen and R is hydrogen or a $C_1$–$C_6$ group, or a pharmaceutically acceptable salt thereof, wherein aryl is phenyl, biphenyl, or naphthyl on a $C_{1-6}$-alkyl substituted phenyl, biphenyl or naphthyl.

2. The compound of claim 1, which is represented by the formula:

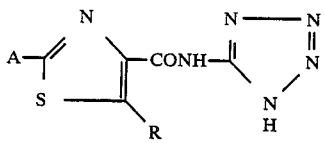

wherein A is a $C_{1-6}$ alkyl group, an aryl group which is unsubstituted or substituted with at least one substituent selected from hydroxy, alkoxy, aryl-($C_{1-6}$)alkoxy, $C_{1-6}$alkylcarbonyloxy, halo-($C_{1-6}$)alkyl, halogen, nitro and amino, and R is hydrogen or a $C_{1-6}$ alkyl group, or a pharmaceutically acceptable salt thereof.

3. The compound of claim 2, in which
A is methyl, or
unsubstituted or mono- or di- or tri substituted phenyl or naphthyl, wherein the substituents are selected from hydroxy, methoxy, stearyloxy, benzyloxy, acetoxy, trifluoromethyl, chloro, nitro and amino, and R is hydrogen, methyl or isopropyl.

4. The compound of claim 1 which is represented by the formula:

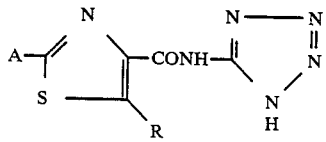

wherein A is a 5- or 6-membered heterocyclic group containing one or two ring hetero atoms selected from the group consisting of oxygen, nitrogen and sulfur or a condensed heterocyclic group consisting of a heterocyclic group as defined above and a benzene nucleus, the heterocyclic group and the condensed heterocyclic group being unsubstituted or substituted with at least one substituent selected from hydroxy, $C_{1-6}$ alkyl, and halogen, and R is hydrogen or a $C_{1-6}$ alkyl group, or a pharmaceutically acceptable salt thereof.

5. The compound of claim 4, in which A is unsubstituted or mono-substituted furyl, thienyl, pyridyl, pyrazinyl piperadinyl or quinolyl, wherein the substituent is selected from hydroxy, methyl and bromo, and R is hydrogen or methyl.

6. The compound according to claim 1 wherein the aryl, heterocyclic and condensed heterocyclic groups are independently unsubstituted, or mono-, di, or tri-substituted.

7. A pharmaceutical composition for the treatment or prophylaxis of allergic diseases which comprises a therapeutically or prophylactically anti-allergic effective amount of the compound according to claim 1 or a pharmaceutically acceptable salt thereof in association with a pharmaceutically acceptable carrier or diluent.

8. A pharmaceutical composition useful in the treatment of allergic diseases which comprises an anti-allergic effective amount of at least one compound according to claim 1 or a pharmaceutically acceptable salt thereof in association with a pharmaceutically acceptable carrier or diluent.

* * * * *

UNITED STATES PATENT AND TRADEMARK OFFICE
CERTIFICATE OF CORRECTION

PATENT NO. : 4,879,295

DATED : November 7, 1989

INVENTOR(S) : Junji Yoshinaga, et al.

It is certified that error appears in the above-identified patent and that said Letters Patent is hereby corrected as shown below:

Column 7, line 33: "(12.6 g)" should read as --(13.6 g)--

Column 9, line 16: "(2-hydroxyphehyl)" should read as --(2-hydroxyphenyl)--

Column 10, line 3: "the" should read as --The--

Column 17, line 20: "bloods" should read as --blood--

Column 26, line 63: "$C_1-C_6$ group" should read as --$C_1-C_6$ alkyl group--

Signed and Sealed this

First Day of October, 1991

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,879,295
DATED : November 7, 1989
INVENTOR(S) : Junji Yoshinaga, et al.

It is certified that error appears in the above-identified patent and that said Letters Patent is hereby corrected as shown below:

On Title Page, Section [54]: "THIAZOLECARBOXYAMIDE" should read as --THIAZOLECARBOXAMIDE--.

On Title Page, Section [75]: "Shoyaki" should read as --Shogaki--.

Column 1, Line 1, "THIAZOLECARBOXYAMIDE" should read as --THIAZOLECARBOXAMIDE--.

Column 1, Line 27, "derivates" should read as --derivatives--.

Column 1, Line 35, "(1086)" should read as (1986).

Column 1, Line 54, "substituted" should read as --substituent--.

Column 2, Line 14, "aminotetazole" should read as --aminotetrazole--.

Column 2, Line 17, 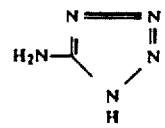

should read as 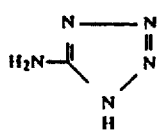

Column 2, Line 23, "ractive" should read as --reactive--.

UNITED STATES PATENT AND TRADEMARK OFFICE
CERTIFICATE OF CORRECTION

PATENT NO. : 4,879,295

DATED : November 7, 1989

INVENTOR(S) : Junji Yoshinaga, et al.

It is certified that error appears in the above-identified patent and that said Letters Patent is hereby corrected as shown below:

Column 2, Line 52, "DEATAILED" should read as --DETAILED--.

Column 4, Line 37, "hydride" should read as --anhydride--.

Column 9, Line 21, "hours" should read as --hour--.

Column 13, Line 1, "wrere" should read as --were--.

Column 13, Line 12, "hydrogeneted" should read as --hydrogenated--.

Column 14, Line 60, "2-[(t-butyl)phenyl]" should read as --2-[4-(t-butyl)phenyl]--.

Signed and Sealed this

Fourth Day of February, 1992

Attest:

HARRY F. MANBECK, JR.

*Attesting Officer*       *Commissioner of Patents and Trademarks*

UNITED STATES PATENT AND TRADEMARK OFFICE
CERTIFICATE OF CORRECTION

PATENT NO. : 4,879,295

DATED : November 7, 1989

INVENTOR(S) : Junji Yoshinaga, et al.

It is certified that error appears in the above-identified patent and that said Letters Patent is hereby corrected as shown below:

Column 26, line 65, Claim 1: "naphthyl on a" should read as --naphthyl or a--

Signed and Sealed this

Fifteenth Day of December, 1992

Attest:

DOUGLAS B. COMER

Attesting Officer

Acting Commissioner of Patents and Trademarks